(12) United States Patent
Kennard

(10) Patent No.: US 8,292,875 B2
(45) Date of Patent: Oct. 23, 2012

(54) FLUID DELIVERY DEVICE

(76) Inventor: Clay Kennard, Oklahoma City, OK (US)

( * ) Notice: Subject to any disclaimer, the term of this patent is extended or adjusted under 35 U.S.C. 154(b) by 211 days.

(21) Appl. No.: 11/854,029

(22) Filed: Sep. 12, 2007

(65) Prior Publication Data

US 2008/0065023 A1  Mar. 13, 2008

Related U.S. Application Data

(60) Provisional application No. 60/843,877, filed on Sep. 12, 2006, provisional application No. 60/860,138, filed on Nov. 20, 2006, provisional application No. 60/909,612, filed on Apr. 2, 2007.

(51) Int. Cl.
*A61M 25/16* (2006.01)
(52) U.S. Cl. .......... 604/538; 604/533; 604/905
(58) Field of Classification Search .......... 604/240, 604/243, 326, 533–539, 905, 921, 910, 516
See application file for complete search history.

(56) References Cited

U.S. PATENT DOCUMENTS

| | | | | |
|---|---|---|---|---|
| 5,267,983 A * | 12/1993 | Oilschlager et al. | ......... | 604/533 |
| 5,429,620 A * | 7/1995 | Davis | ............. | 604/538 |
| 5,776,117 A * | 7/1998 | Haselhorst et al. | .......... | 604/533 |
| 6,042,569 A * | 3/2000 | Finch et al. | .................. | 604/175 |
| 6,582,395 B1 * | 6/2003 | Burkett et al. | ............ | 604/96.01 |
| 6,610,045 B2 | 8/2003 | Chavez | | |
| 2004/0124389 A1 | 7/2004 | Phillips | | |
| 2006/0047251 A1 * | 3/2006 | Bickford Smith et al. | ... | 604/240 |
| 2006/0064065 A1 * | 3/2006 | Russo | ............. | 604/256 |
| 2007/0060898 A1 * | 3/2007 | Shaughnessy et al. | ....... | 604/284 |

FOREIGN PATENT DOCUMENTS

EP  0097054 B1  9/1988
EP  1426069 A1  6/2004

\* cited by examiner

*Primary Examiner* — Kevin C Sirmons
*Assistant Examiner* — Kami A Bosworth

(57) ABSTRACT

A fluid delivery device and system is operable to fluidly couple a pair of fluid delivery conduits. One embodiment includes a fluid delivery device sized to meet ANSI/AAMI ID54:1996(R) 2005 and not mate with ANSI/HIMA MD70.1 or ISO 594/1 and ISO 594/2 standards for intravenous ports and connectors to prevent accidental intravenous delivery of fluids intended for enteral delivery.

17 Claims, 14 Drawing Sheets

Fluid delivery device 100

Fluid delivery device 100

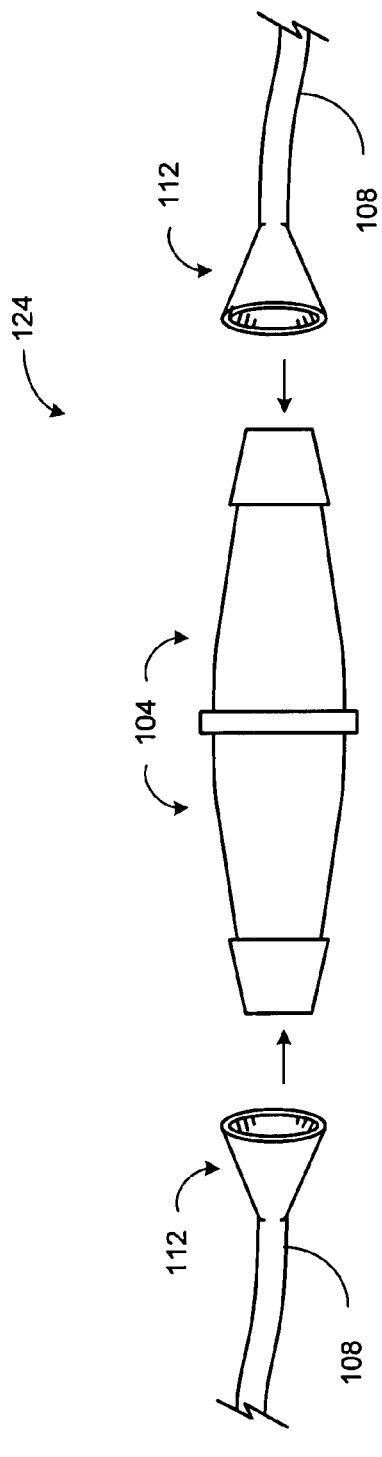
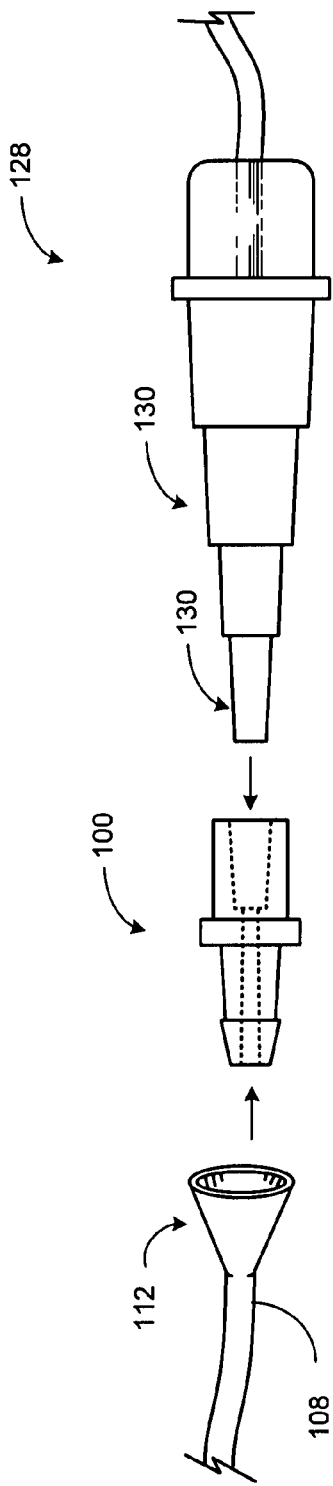

Fluid delivery system with fluid delivery device 100 and matching connector 132

Fluid delivery system
150

Locking mechanism of female connector end of a device

Female connector end adhesive or bonding agent

Feeding cap

Enteral tip

Enteral tip circular disk barb

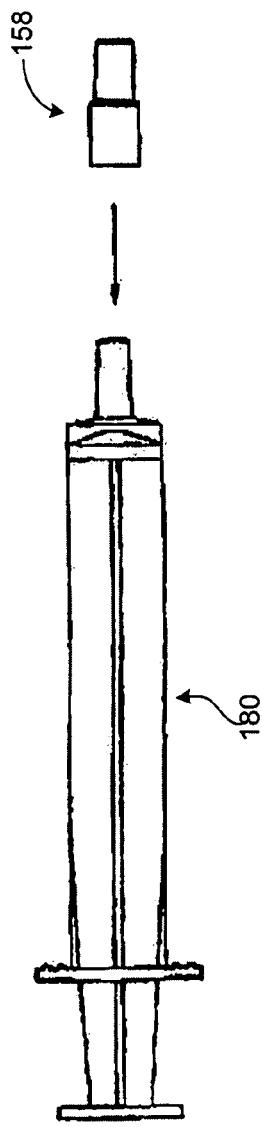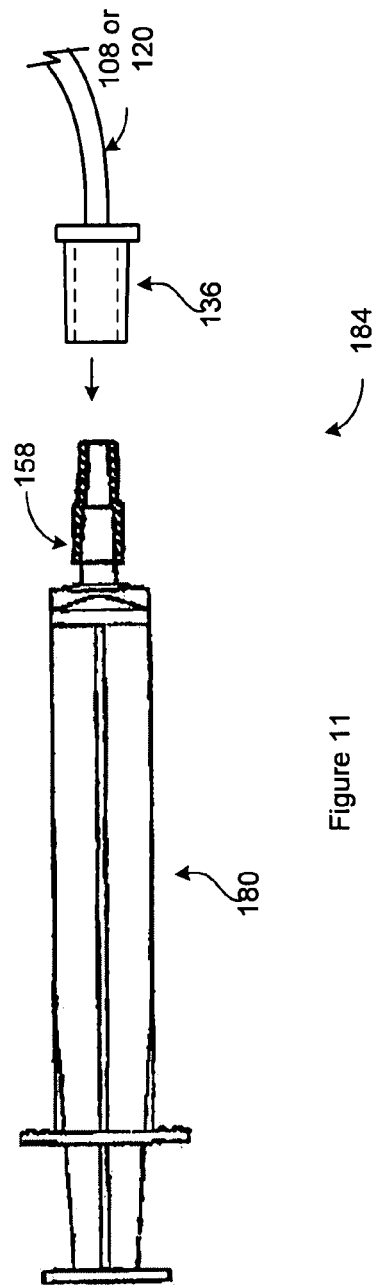
Figure 10
Syringe and enteral tip of enteral feeding system
Figure 11
Enteral feeding system Enteral tip Enteral tip

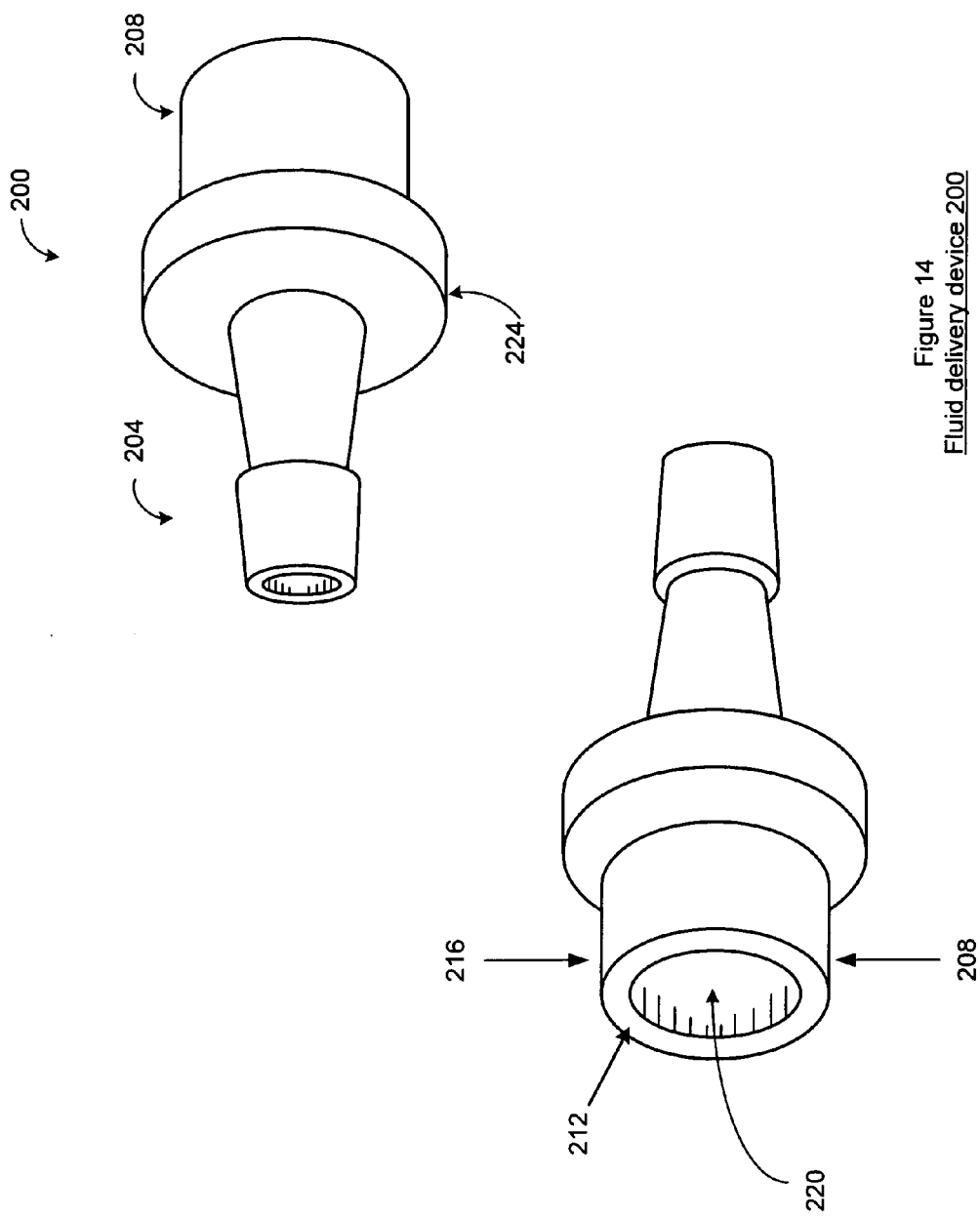

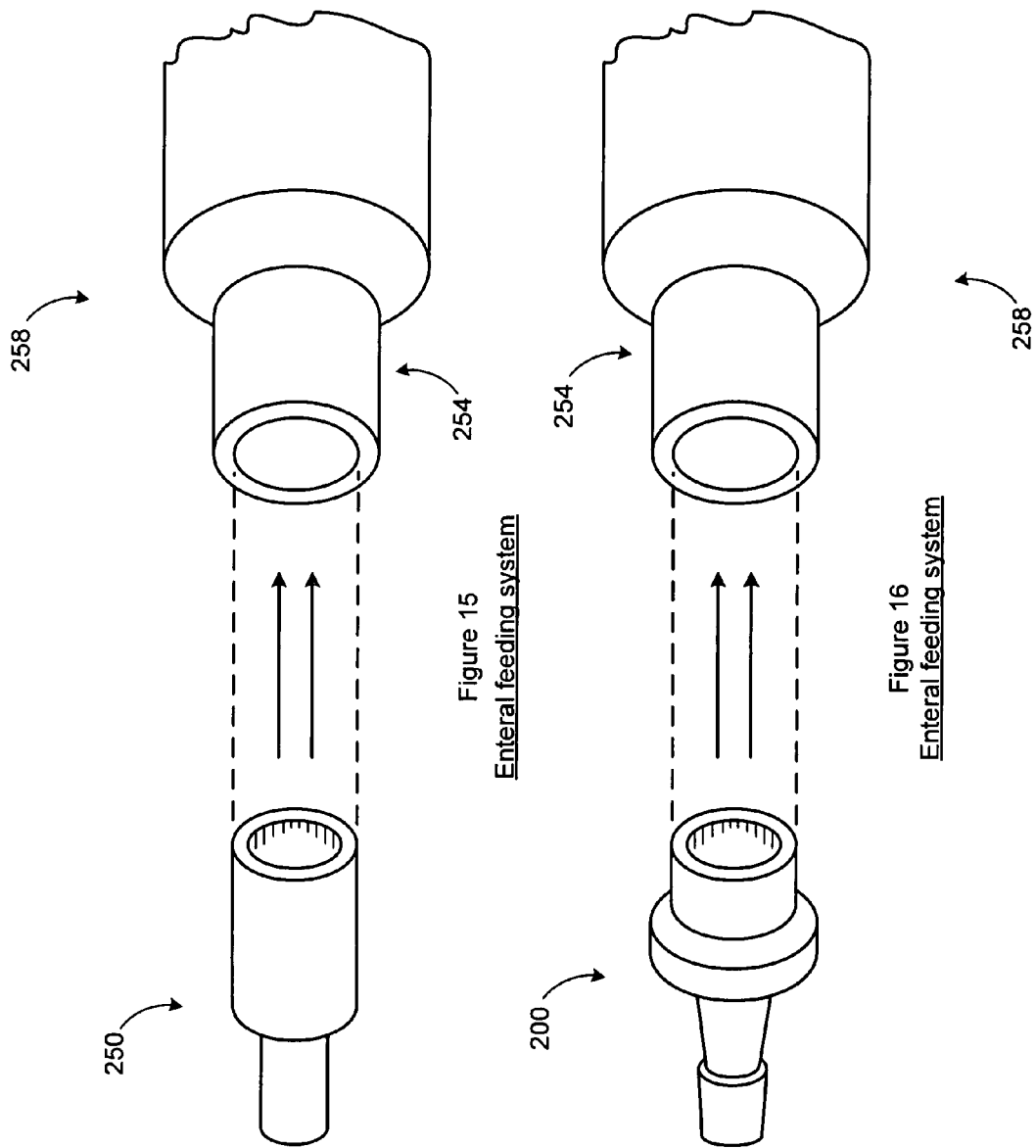

FLUID DELIVERY DEVICE

CROSS REFERENCE TO RELATED PATENTS

This U.S. application for patent claims the benefit of the following U.S. Provisional Patent Applications, which are incorporated herein by reference for all purposes:
1) U.S. Provisional Patent Application having a Ser. No. of 60/843,877 and a filing date of Sep. 12, 2006;
2) U.S. Provisional Patent Application having a Ser. No. of 60/860,138 and a filing date of Nov. 20, 2006; and
3) U.S. Provisional Patent Application having a Ser. No. of 60/909,612 and a filing date of Apr. 2, 2007.

BACKGROUND

1. Technical Field

The present invention relates to medical devices and, more particularly, to connectors for intravenous and enteral delivery of medicinal and nutritional flows.

2. Related Art

Fluid delivery systems are known to fill a great necessity for delivery of medicine and nutrients to ill and disabled patients in many settings especially hospitals and health care facilities. For example, in neo-natal units, infants are often fed enterally (e.g., a tube inserted in the mouth or nasal opening (nare) and through the trachea for delivery of the fluid to the stomach or intestinal region of the body) and are also provided medication and other fluids intravenously.

One particular problem includes interfacing differing devices to enable said devices to mechanically couple to deliver a food, sustenance or medicine. For example, formula and breast milk are often delivered by syringe into an enteral delivery system for delivery to the infants stomach. Tragically, however, through too common of oversight, infants are accidentally killed when a syringe with nutritional food is coupled to an I.V. port and injected into the blood stream. Milk delivered to the heart, however, is usually fatal to the infant.

One reason for such mistakes relates to the technology for delivering food and medicine. Too often, syringes that are used for either delivering food to an enteral delivery system may also be used for delivery of medicine or fluid to an I.V. system. Because these syringes are technically compatible with either system, tragic mistakes are possible and may even be expected.

Thus, a need exists for a device that is compatible with common delivery systems to allow such systems to fluidly communicate. A further need exists for fluid communication devices that are operable to provide safeguards to avoid tragic mistakes.

SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE DRAWINGS

A better understanding of the present invention can be obtained when the following detailed description of the preferred embodiment is considered with the following drawings, in which:

FIG. 2 is an illustration of an alternate embodiment with two barbed ends;

FIG. 3 is an illustration of a device mating with a multi-sized connector;

FIG. 10 is a block diagram that illustrates a syringe and a separate fluid delivery device;

FIG. 11 is a block diagram that illustrates a syringe engaged to a fluid delivery device;

FIG. 14 is a block diagram that illustrates a fluid delivery device formed according to one embodiment of the invention;

FIG. 15 is a block diagram that illustrates a fluid delivery device defining an outer diameter that matingly engages an opening of a male end of a syringe of a second size;

FIG. 16 illustrates an alternate embodiment of a fluid delivery device being inserted into the end of a syringe;

DETAILED DESCRIPTION OF THE DRAWINGS

Figure 1:
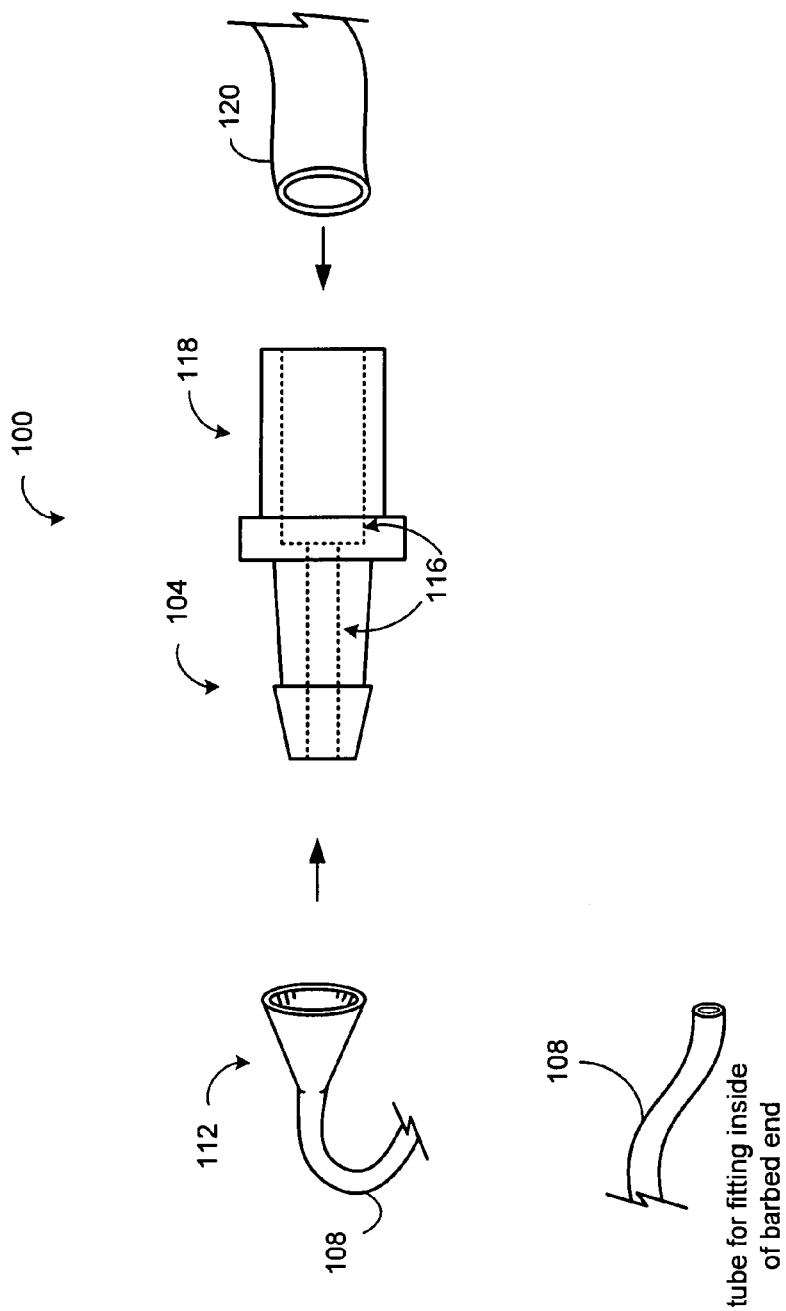
FIG. 1 is an illustration of a device for connecting two tubes.

FIG. 1 is a fluid delivery system that includes a device for connecting two tubes. A fluid delivery device 100 includes a barbed end 104 that forms a barbed outer surface for receiving and fixedly attaching to a tube 108 with an overmold end 112 or region for attaching over barbed end 104. As may be seen from examining FIG. 1, the barbed end 104 comprises a tapered projection having only a single barb extending therefrom. The barbed end 104 further includes a conduit 116 for conducting fluids. Conduit 116 is sized to match an outer diameter of a specified tube (e.g., tube 108) used for medical applications. The tube 108 may then be permanently attached with adhesive or bonding agents. The tube is typically PVC or polyurethane. The opposite end of the barbed end 104, in one embodiment, is a female connector end 118 sized to receive a tube 120 and to match the diameter of the tube 120 for which it is sized to receive. Again, the tube 120 is a specified tube used in the medical community and may be the same or a different size than tube 108 that is received within the barbed end 104 (as shown in FIG. 1).

Thus, a first fluid delivery device for connecting to a tube for enteral delivery of fluids comprises a first connector end comprising a barbed connector end operable to securely couple to an overmold region of a first tube made of a first specified material and further defining an internal conduit sized to receive a second tube made of a second specified material having a specified outer diameter. The first fluid delivery device further includes a second connector end for receiving a third tube having a second specified outer diameter formed of a third specified material.

In one embodiment, the second and third specified material are formed from one of medical PVC or polyurethane. Thus, the second and third tubes made from the second and third materials may be composed of the same or of different material. Generally, though, they are different from the first material which forms the overmold portion of the tube and couples to the barbed end. In one embodiment, the first specified material from which tube 108 is formed comprises a silicon based tubing material.

The second connector end (female connector end 118) of the first fluid delivery device is formed to receive a tube having a second specified outer diameter, but also defines a size to prevent mating with standard sized I.V. connectors and ports (for example, to not mate with standard connector or port sizes for I.V.'s defined by the American National Standards Institute (e.g., standards similar to ANSI/HIMA MD70.1 or ISO 594/1 and ISO 594/2 standards). Thus, the embodiment of the invention includes any dimension that is not compatible with standard sized I.V. connectors and ports to keep the two from being inadvertently coupled mechanically.

In one embodiment, the second connector end defines a tubular shape with a diameter and thickness to cause the second end to butt against and not engage a Luer (protruding flange) of a standard syringe for delivery of medicine (e.g., I.V. delivery). Thus, the diameter of the second connector end is greater than an inner diameter of a Luer (which is typically made to a standard size or dimension) and a wall thickness of the second connector is sufficient to define an inner diameter that is smaller than a diameter of the Luer. As such, the second connector end may only butt up against a Luer and cannot engage it. Further, the inner diameter of the second connector end is greater in diameter in the described embodiment than a male end of a standard syringe or I.V. connector to prevent the second connector end from matingly and snugly engaging the male end of a syringe made for medical delivery.

In one embodiment, the tube 120 is permanently coupled to an interior wall of the second connector end when received by the second connector end with a mechanical, adhesive, or bonding mechanism or agent. Similarly tube 120 may be received by the internal conduit of the barbed end 104 and may be permanently secured thereto by way of a mechanical, adhesive, or bonding mechanism or agent. On the other hand, the barbed connector end 104 is operable to securely couple to the overmold region 112 of the tube without adhesive material by way of a compression fit.

As an additional aspect of the embodiment of the present invention, the fluid delivery device includes a second connector that is sized to meet ANSI/AAMI ID54:1996(R) 2005 and not mate with ANSI/HIMA MD70.1 or ISO 594/1 and ISO 594/2 standards for intravenous ports and connectors. While the preferred embodiment contemplates a second connector defining a female connector end, an alternate embodiment includes a male connector end for the second connector that may be inserted into a syringe having a fluid delivery port of a size for receiving such connector for enteral delivery of food and certain medicines that are not for I.V. delivery.

FIG. 2 is an alternate embodiment a fluid delivery system with a first fluid delivery device having two barbed ends. As may be seen, the fluid delivery system includes a connector 124 that has two barbed ends 104 as described in relation to FIG. 1 in this embodiment.

FIG. 3 is a fluid delivery system that includes a fluid delivery device and a multi-sized connector. As may be seen, a multi-sized connector 128 includes a plurality of stepped connector surface areas 130 made to match a corresponding plurality of connectors. In general, connector 128 is for supporting enteral delivery of medication or food. The male connector end of connector 128 is sized to engage the second connector end of fluid delivery device 100, which, as described before, is sized to not engage standard syringes for I.V. delivery of medication.

Figure 4:
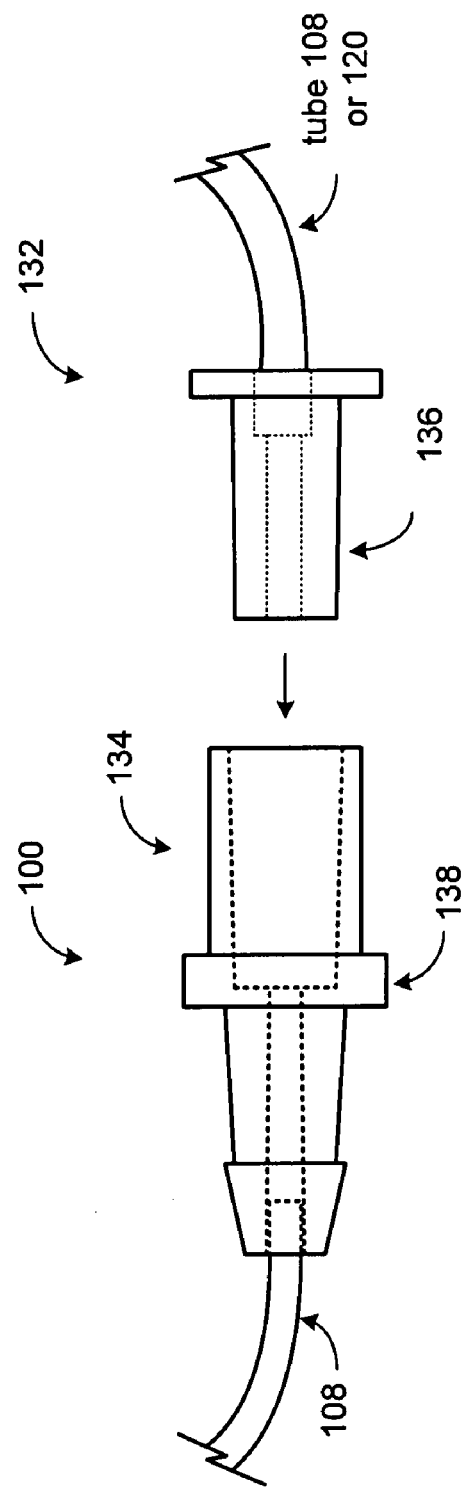
FIG. 4 is an illustration of a device mating with a connector that is then attached to a tube.

FIG. 4 illustrates the fluid delivery device system that includes a fluid delivery device 100 with a matching connector 132 according to one embodiment of the invention. In at least one embodiment, an end 134 of device 100, namely, the non-barbed end of connector 100, is specifically sized to meet ANSI/AAMI ID54:1996(R) 2005 for enteral delivery and not mate with standard (e.g., ANSI/HIMA MD70.1 or ISO 594/1 and ISO 594/2 standards) connector or port sizes for I.V.'s. More specifically, in one embodiment, the non-barbed end is sized to butt against and not overlap or slide within or over a Luer of a syringe for delivering medication while being able to engage a connector end 136 of connector 132 which connector end 136 meets standard ANSI/AAMI ID54:1996(R) 2005.

Each of the tubes 108 and 120 defines an internal diameter sized to define a specified flow rate. Accordingly, the fluid delivery devices 100 of the fluid delivery systems, as shown here and in other Figures, include compatibly sized internal conduits to receive the tubes 108 or 120 that are made to conduct fluids at the specified flow rates. One additional aspect of an embodiment of the device includes a flange 138 extending outward and radially from the first and second connector ends. This flange facilitates handling.

Figure 5:
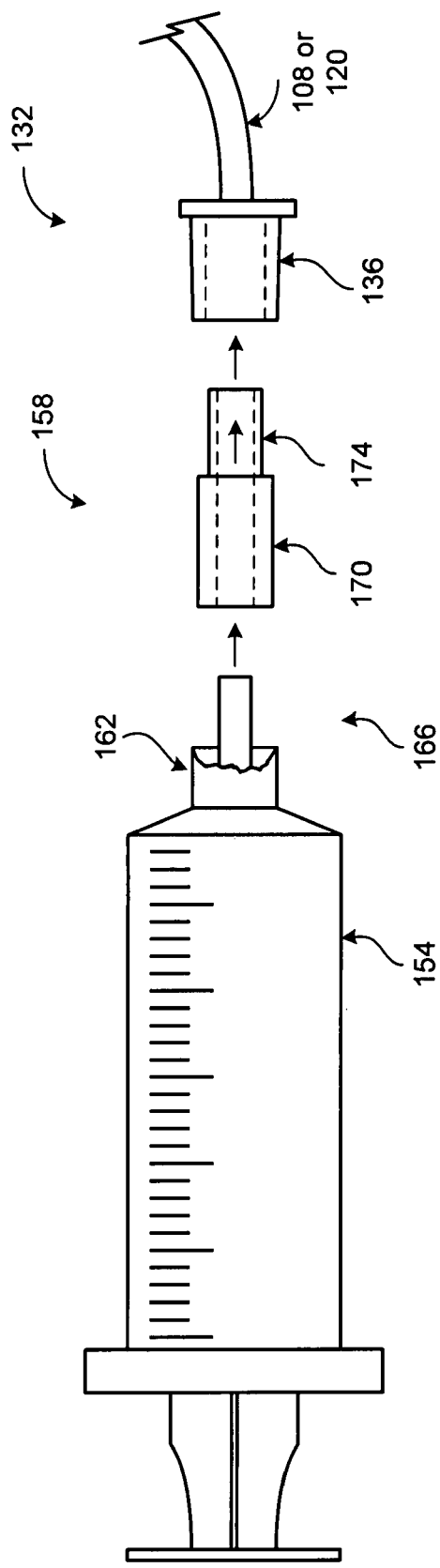
FIG. 5 is an illustration of a device for a syringe.

FIG. 5 illustrates a fluid delivery system according to one embodiment. Generally, a fluid delivery system 150 includes a fluid delivery device, a matching connector, associated tubing and a syringe. The system 150, more specifically, includes a syringe 154 that is for delivery of medicine intravenously. Additionally, system 150 includes a fluid delivery device 158 that forms an interface between syringe 154 and connector 132. Fluid delivery device 158 is made to permanently adhere to syringe 154 and to fit between a Luer 162 and a delivery end 166 of syringe 154. Specifically, device 158 is sized to fit within the Luer 162 of syringe 154 and to form a sealed connection with syringe 154 from which medicine flows. In the described embodiment, the delivery end 166 is a male connector end.

Fluid delivery device 158 includes a female connector end 170 that overlaps the male portion of delivery end 166 of syringe 154. Delivery end 166 of syringe 154 and device 158 are permanently attached. One embodiment of the fluid delivery system 150 includes a locking mechanism for permanent attachment of device 158 to syringe 154. The locking mechanism may be mechanical (e.g., a pin or barb that mechanically grabs the male end of the syringe) or chemical (e.g., an adhesive or bonding agent). A male connector end 174 of device 158 is sized to not mate with standard connectors or ports for I.V.'s as described before. Similarly, one embodiment of connector 132 includes an end 136 that is sized to not engage or mate with standard I.V. ports and connectors.

Thus, fluid delivery device 158 is made especially for permanently connecting to an end of a syringe sized to meet ANSI/HIMA MD70.1 or ISO 594/1 and ISO 594/2 standards for intravenous ports and connectors to create a fluid delivery system that prevents inadvertent I.V. delivery of fluids intended for enteral delivery. For example, a syringe typically includes a male end for delivering fluid stored within a storage chamber of the syringe. As such, once a syringe is chosen for delivering fluids enterally instead of intravenously, permanent attachment of the fluid delivery device 158 reduces the likelihood of dangerous fluids being delivered intravenously. The fluid delivery system 150 comprises any known structure for permanently attaching, adhering or bonding the fluid delivery device to the fluid delivery end of the syringe.

To prevent the syringe with fluids not intended for intravenous delivery from being accidentally coupled to an intravenous fluid delivery port or connector, the fluid delivery device 158 is permanently attached to syringe 154 in the described embodiment of the fluid delivery system 150.

Generally, if a locking mechanism (mechanical structure or chemical element) is not used to make this permanent attachment, an application technique that permanently installs device 158 to a syringe, such as syringe 154, may be used, including spin welding and pressure mounting. In the described embodiment, the fluid delivery system includes, therefore, the syringe 154 (or other syringe), the fluid delivery device 158 permanently attached to syringe 154, connector 132 that is coupled to a tube, and the tube itself. The fluid delivery devices 158 and connector 132 each include fluid delivery ends sized to not mate with standard sized intravenous ports and connectors.

The fluid delivery system 150 comprises any known structure for permanently attaching, adhering or bonding the fluid delivery device to the fluid delivery end of the syringe in addition to those described. As such, one aspect of the embodiments of the invention is that, once a syringe is chosen for delivering fluids enterally instead of intravenously, a system and method includes permanent attachment of a fluid delivery device to a syringe to reduce the likelihood of dangerous fluids being delivered intravenously.

The embodiments of the locking mechanism include but are not limited to at least one protruding barb, originating from an interior surface of the female connector end, that extends towards an axial center of the female connector end, and is operably sized to receive and pass the male end of the syringe only in a receiving direction. Alternatively, the locking mechanism comprises an adhesive material, a heat activated bonding agent, or a latching mechanism. For example, an ultra-violet (U.V.) agent may be applied that, when exposed to U.V. light transmitted through the translucent material of a syringe, causes the fluid delivery device to permanently adhere to the syringe fluid delivery port.

In an alternate embodiment, instead of utilizing locking mechanisms, the fluid delivery systems comprise a syringe and a fluid delivery device that are permanently adhered to each other through a mechanical or other process. In one embodiment of the invention, for example, the fluid delivery device 158 is permanently adhered to the Luer 162 of the syringe 154 using a technique known as "spin welding" in which the surfaces of the syringe and fluid delivery device melt to permanently fuse the delivery device to the syringe. The fused portion resulting from such "spin welding" thus becomes the locking mechanism. Alternately, the fluid delivery system may comprise a pressure mounting to prevent separation of the fluid delivery device 158 and the male end of the syringe 154 wherein machinery permanently joins the syringe and the fluid delivery device in a manner in which a mating pressure causes the syringe and fluid delivery device to be permanently adhered.

While the fluid delivery device 158 may be made with any combination of male and female connectors as an input port, one described embodiment includes a female connector end sized to receive and mate with a male end of a syringe. The permanent attachment of the fluid delivery device 158 to the syringe 154 is particularly important since the male connector end of the permanently attached fluid delivery device is sized to meet ANSI/AAMI ID54:1996(R) 2005 for enteral delivery and not mate with ANSI/HIMA MD70.1 or ISO 594/1 and ISO 594/2 standards for intravenous ports and connectors. Thus, once an I.V. syringe is chosen for enteral delivery of food or medicine, it cannot accidentally be coupled to an I.V. port to accidentally introduce dangerous fluids to the blood stream. Moreover, the female connector end of the device 158 defines an outer dimension or size made to fit within and engage with a protruding flange (Luer) that surrounds the protruding male end of the syringe to support the permanent and sealed attachment to the syringe.

One embodiment of the fluid delivery device 158 includes a female connector end having an outer diameter that is sized to matingly fit within a port of a syringe of a second size. For example, I.V. syringes typically are made in one of two sizes. Thus, an alternate fluid delivery system includes a fluid delivery device 158 that is formed to matingly be received by a male end of a syringe having an outer diameter of a first size (or type) which is typically for I.V. applications and to also matingly fit into a male end of a second type of syringe for enteral delivery of food and medicine defining an inner diameter of a second size.

Thus, the embodiments of the invention for fluid delivery systems include a syringe having a chamber for temporarily holding a fluid intended for enteral delivery to a patient and a permanently attached fluid delivery device fluidly connected to the chamber for delivering the fluid to a tube wherein the male connector end of the fluid delivery device is sized to meet ANSI/AAMI ID54:1996(R) 2005 and not mate with ANSI/HIMA MD70.1 or ISO 594/1 and ISO 594/2 standards for intravenous ports and connectors.

Figure 6:
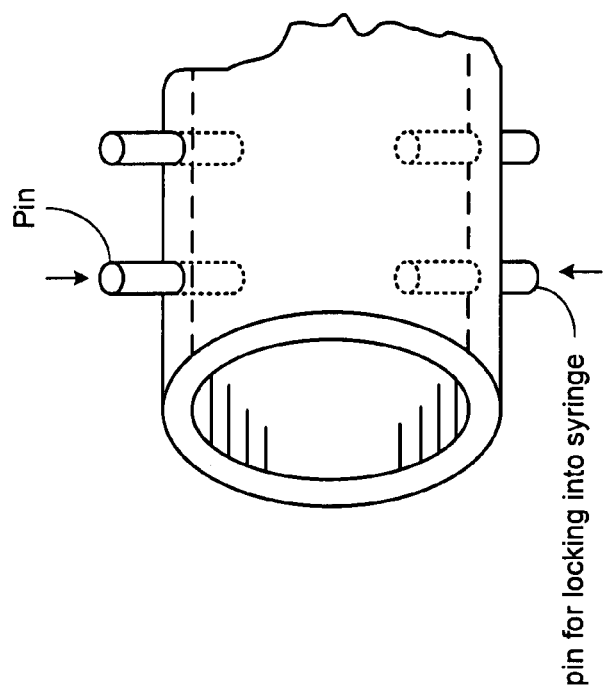
FIGS. 6 and 7 are illustrations of locking mechanisms.
Figure 7:
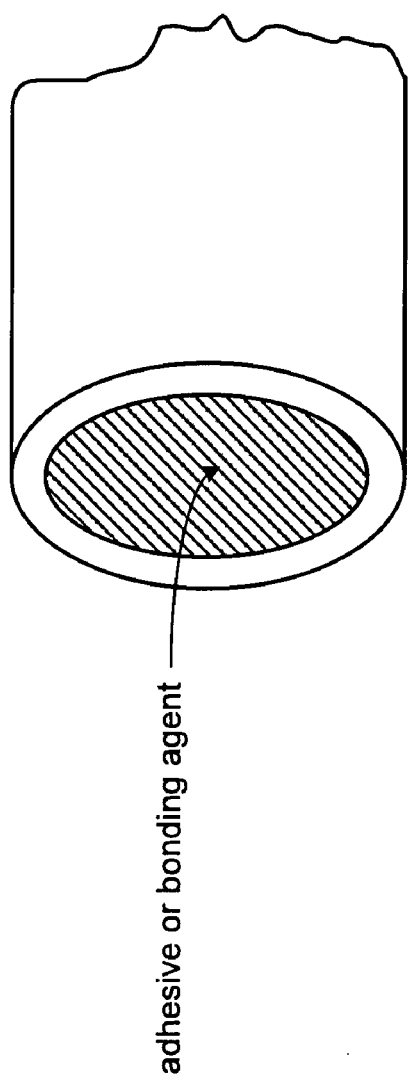

FIGS. 6 and 7 illustrate embodiments of the invention for locking mechanisms for coupling a fluid delivery device to a syringe. In particular, FIG. 6 illustrates a locking mechanism of a female connector end that includes pins for locking two devices. FIG. 7 illustrates a female connector end with an adhesive lining at least a portion of an inner surface sized to mate with a fluid delivery device to allow the fluid delivery device to be permanently attached thereto.

Figure 8:
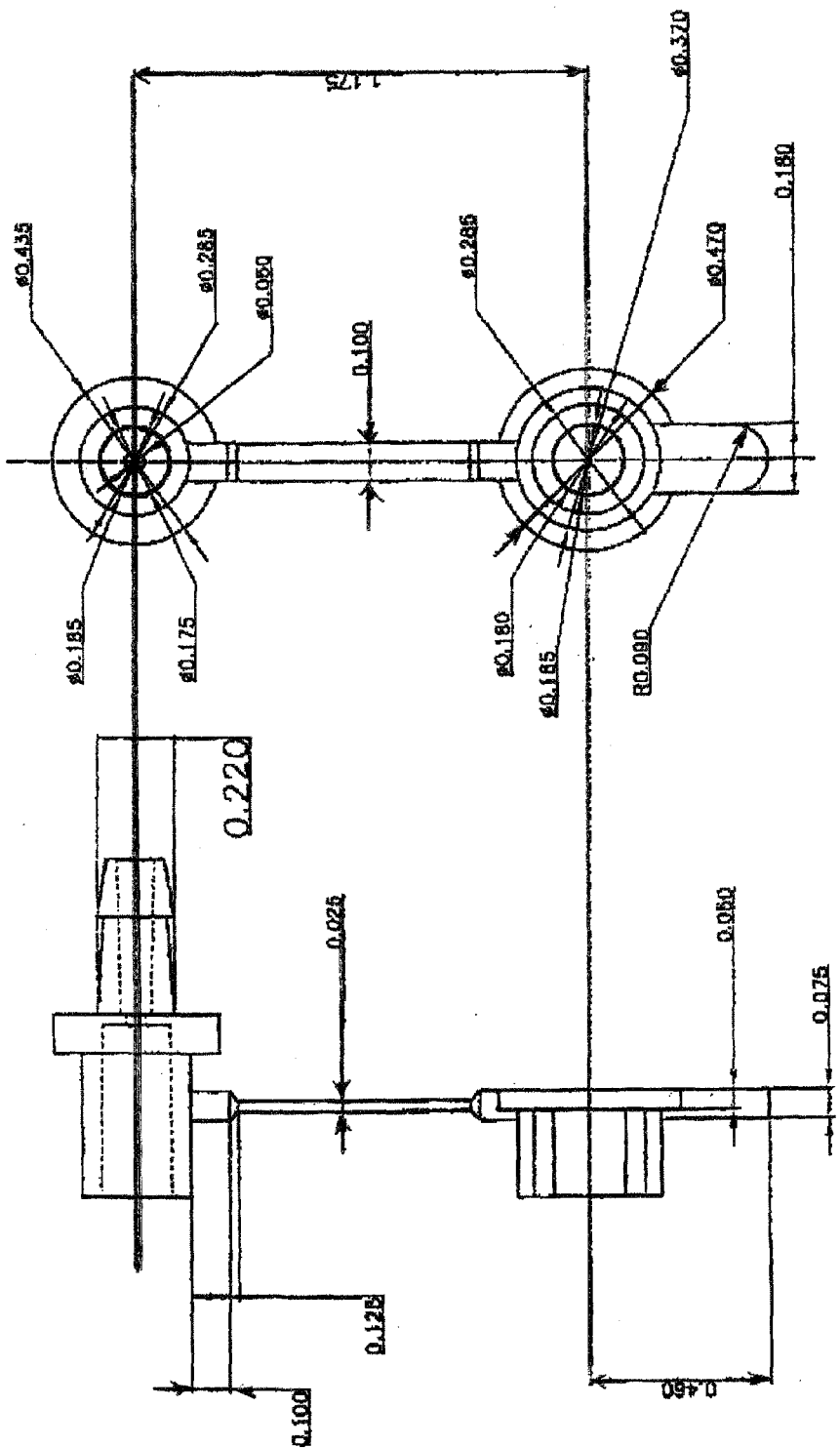
FIG. 8 is an illustration of an exemplary diagram of a first device of a connector.

FIG. 8 is an exemplary diagram of the first device described above (the fluid delivery device 100) with specific dimensions shown for one particular embodiment of the invention. FIG. 8 is provided to give exact dimensions of one embodiment of the invention. It should be note that the units for this drawing are in inches. The symbol "Ø" before a dimension reflects that the dimension is a diameter. The letter "R" reflects a curvature radius dimension.

Figure 9A:
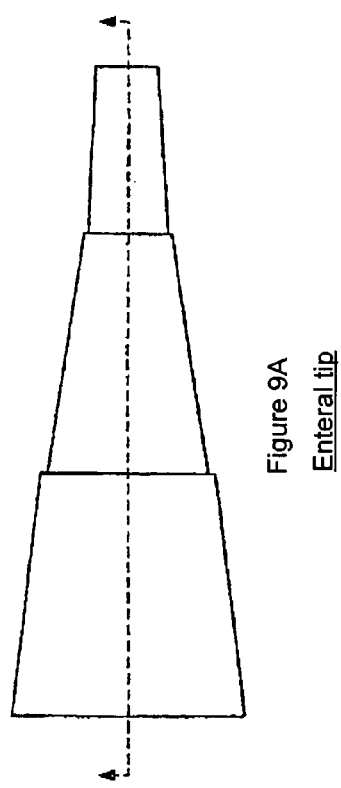
FIGS. 9A and 9B are illustrations of a device that attaches to a syringe.
Figure 9B:
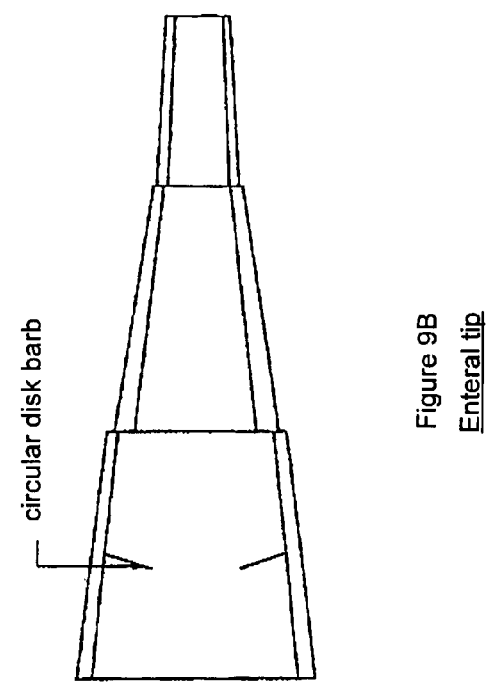

FIGS. 9A and 9B are illustrations of an additional embodiment of a fluid delivery device that attaches to a syringe. While FIG. 9A illustrates a side view of the fluid delivery device (an enteral tip), FIG. 9B illustrates a cutaway view of the fluid delivery device. The outer portion is formed to engage a syringe with a Luer and to mate with tubes of different overmolded dimensions while an internal conduit portion includes a circular disk barb that is operable to permanently adhere to a protruding male end of a syringe that is received by the fluid delivery device.

FIG. 10 is a diagram that illustrates a fluid delivery system that includes a syringe and a separate fluid delivery device (enteral tip) according to one embodiment of the invention. As may be seen, a syringe 180 and fluid delivery device 158 are shown unattached. The fluid delivery device 158 includes a female connector end that is sized to matingly receive the male end of the syringe 180 and comprises (wherein the fluid delivery device forms) an output port (male connector end) that is sized to not mate with I.V. ports as described herein this specification.

FIG. 11 is a diagram of a fluid delivery system (enteral feeding system) that illustrates the syringe 180 permanently engaged to fluid delivery device 158 in addition to connector 132 and tube 108 or 120 to form a fluid delivery system 184. In one embodiment, the fluid delivery device 158 is overmolded onto the syringe 180 male end to permanently adhere the device 158 to the syringe 180. Generally, though, any method of permanently attaching fluid delivery device 158 to syringe 180, including spin welding and other bonding techniques, may be used. Further, the fluid delivery device 158 is formed of a color to identify the fluid delivery system 184 and syringe 180 as being designated for non-intravenous applications. Embodiments include orange and purple for said colors though other colors may be used. All described methods of attaching the fluid delivery device 158 to syringe 180 to create a fluid delivery system may be used as well as any known equivalent including spin welding and other techniques and structures described herein.

Figure 12:
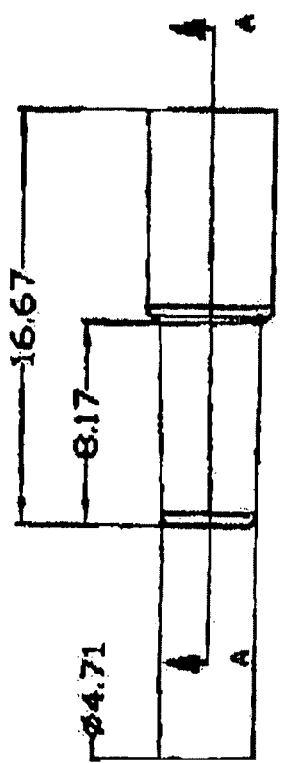
FIGS. 12 and 13 are block diagrams that illustrate various aspects and embodiments of a fluid delivery device formed to be permanently mated with a syringe.
Figure 13:
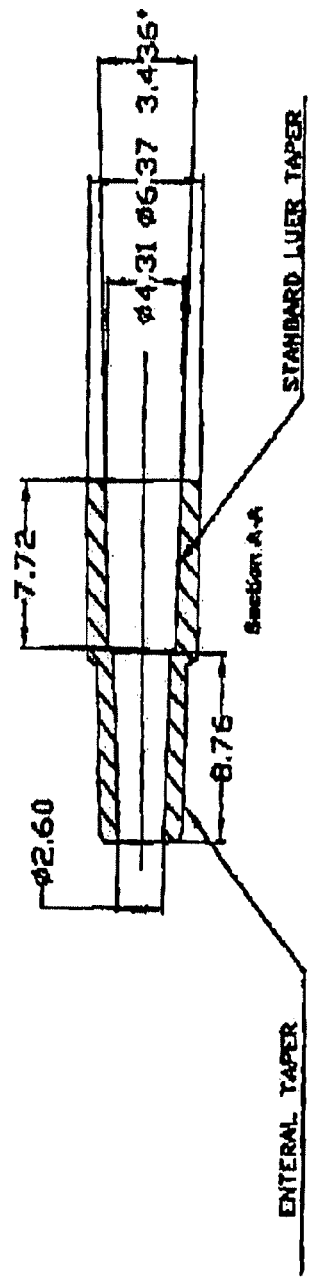

FIGS. 12 and 13 are diagrams that illustrate various aspects and embodiments of the fluid delivery device 184 (enteral tips) formed to be permanently mated with a syringe. FIGS. 12 and 13 are provided to give exact dimensions of one embodiment of the invention. It should be note that the units for this drawing are in millimeters. The symbol "Ø" before a dimension reflects that the dimension is a diameter. The letter "R" reflects a curvature radius dimension.

FIG. 14 is a diagram that illustrates a fluid delivery device formed according to one embodiment of the invention. Fluid delivery device 200 of FIG. 14 is similar to the fluid delivery device 100 of FIG. 1 except that device 200 is sized to receive a male end of a syringe. It should be noted that the various aspects of the fluid delivery device 200 for FIG. 14 may be modified according to the specific application and may include aspects of other embodiments shown herein the present Figures and Description. A first end 204 (output end) of fluid delivery device 200 is sized to fit enteral fluid delivery ports and to not fit with I.V. fluid delivery ports whose dimension have been described elsewhere in this specification. A second end 208 has a wall thickness 212 and outer diameter 216 sized to not accept a syringe with a Luer connector as shown, for example, in FIG. 5.

In one embodiment, the second end 208 defines an internal opening 220 sized to receive and mate with a male end of an I.V. syringe having a first dimension for the diameter. In an alternate embodiment, the second end 208 defines an internal opening 220 sized to be larger than a male end of a first dimension for the diameter of an I.V. syringe to prevent the second end 208 of the fluid delivery device from matingly receiving the male end of the syringe of the first size (I.V. syringes). Thus, this alternate embodiment is for use with syringes other than the most common I.V. syringes that are for applying medicine to a patient. Further, the fluid delivery device 200 is formed of a non-clear color such as orange or purple. Other colors such as blue, red, green or black, for example, may also be used. These colors are used to indicate that the fluid delivery system is not for I.V. applications.

In yet another embodiment of the invention, the outer dimension of end 208 (its diameter) is sized to matingly fit into and be permanently adhered to a port of a syringe having an output end of a second size. Finally, it may be seen that fluid delivery device 200 includes a flange 224 to facilitate handling.

FIG. 15 is a diagram that illustrates an enteral feeding system that includes a fluid delivery device 250 defining an outer diameter that matingly engages an opening of a male end of a syringe of a second size (or second type of syringe) and the corresponding syringe. Here, the fluid delivery device 250 is inserted into the output male end 254 of a syringe 258 and then is permanently adhered thereto. This embodiment of a syringe and fluid delivery device, for example, is often permanently adhered to each other with the spin welding technique mentioned previously to create a fluid delivery system.

FIG. 16 illustrates the alternate embodiment of fluid delivery device 200 being inserted into end 254 of syringe 258.

Figure 17:
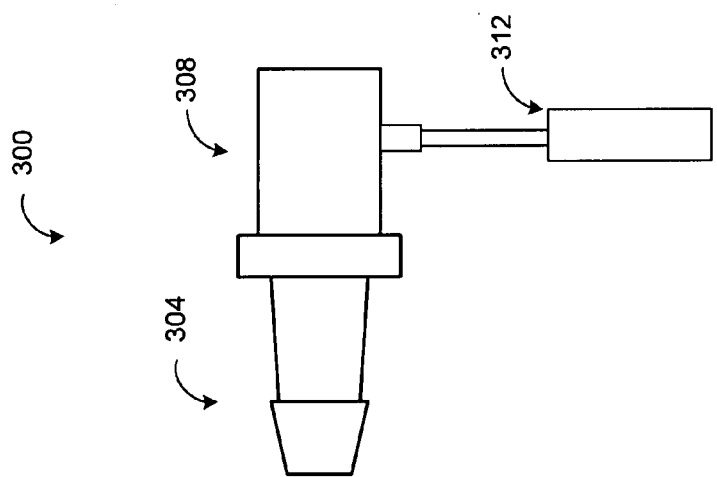
FIG. 17 is a diagram illustrating a layout of a feeding cap according to one embodiment of the invention.

FIG. 17 is a diagram illustrating a layout of a feeding cap according to one embodiment of the invention. As may be seen, a feeding cap 300 includes an output end 304 (barbed male end), a receiving end 308 (female end) and a permanently attached cap 312.

One important aspect is that the receiving end of the feeding cap is sized to not allow a syringe for I.V. applications with a Luer connector to matingly engage the feeding cap. Additionally, the opening for receiving a syringe male end is sized to be larger than an I.V. syringe male end having a smaller standard diameter (first type of syringe) for I.V. syringes and is further sized to be smaller than the larger standard diameter (second type of syringe) for I.V. syringes. More generally, the opening is sized to not matingly engage any male end of a syringe for I.V. applications. On the other hand, the input port of the feeding cap is sized to receive and engage the output end of the fluid delivery devices for enteral applications including, for example, fluid delivery device 158 of FIG. 5, the fluid delivery device of FIGS. 9A and 9B, fluid delivery device 184 of FIGS. 10-13, and fluid delivery device 200 of FIGS. 14-15.

Figure 18:
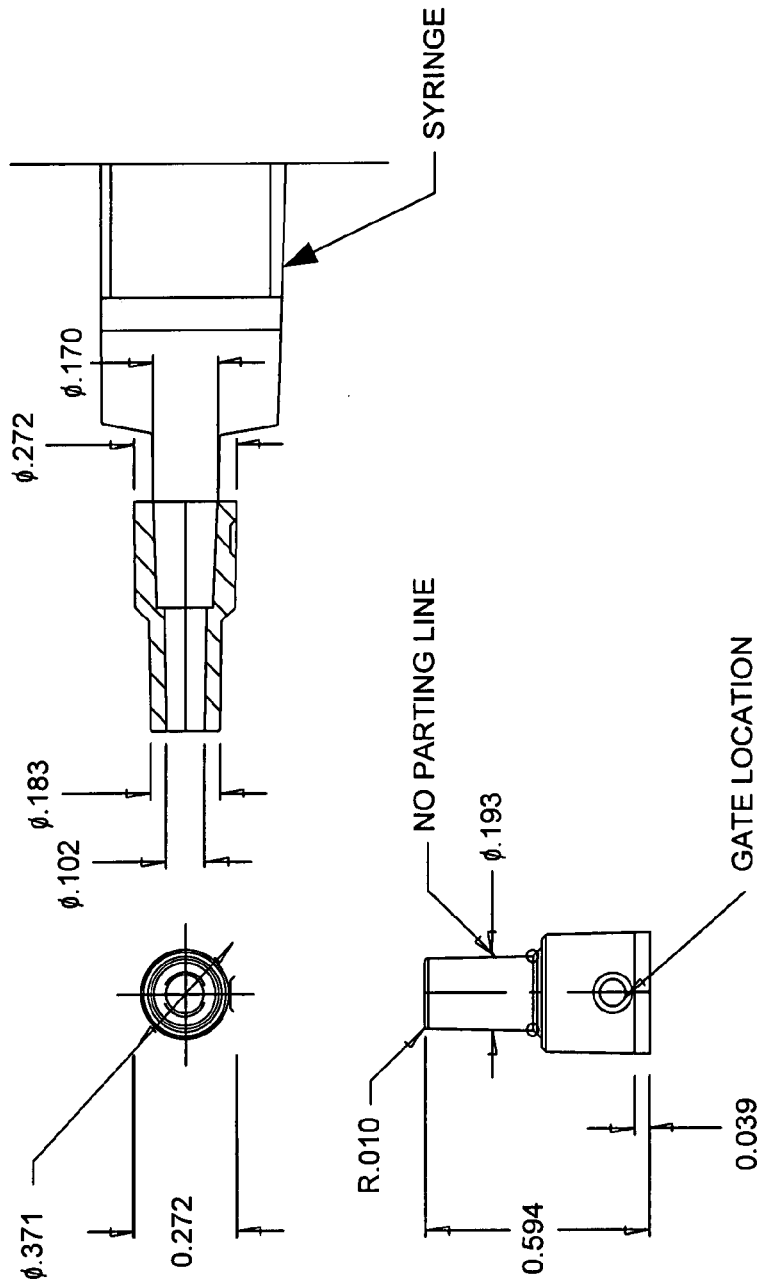
FIG. 18 is an illustration of a specific embodiment of the invention of an enteral tip for permanently mounting onto a syringe.

FIG. 18 is an illustration of a specific embodiment of the invention of an enteral tip for permanently mounting onto a syringe. In particular, the enteral tip is, in this embodiment, overmolded onto the syringe to permanently convert the syringe to enteral feeding purposes and to render the syringe incompatible for I.V. use. Specifically, the output end of the enteral tip shown is made with to not be able to engage with standard ports and connectors for I.V. delivery of medication as has been discussed in relation to prior figures. FIG. 18 is provided to give exact dimensions of one embodiment of the invention. It should be note that the units for this drawing are in inches. The symbol "Ø" before a dimension reflects that the dimension is a diameter. The letter "R" reflects a curvature radius dimension.

While the invention is susceptible to various modifications and alternative forms, specific embodiments thereof have been shown by way of example in the drawings and detailed description. It should be understood, however, that the drawings and detailed description thereto are not intended to limit the invention to the particular form disclosed, but, on the contrary, the invention is to cover all modifications, equivalents and alternatives falling within the spirit and scope of the present invention as defined by the claims. As may be seen, the described embodiments may be modified in many different ways without departing from the scope or teachings of the invention.

The invention claimed is:

1. A fluid delivery system, comprising:
at least one of a first tube and a second tube;
a third tube;
a connector for use in enteral feeding applications configured to connect to the first, second and third tubes and having only a first connector end and a second connector end wherein the first and second connector ends are disposed in a substantially anti-parallel manner;
the first connector end comprising:
a tapered projection having only a single barb extending therefrom;
an internal conduit sized to receive the second tube such that the second tube can be inserted into and matingly engage the first connector end; and wherein the first connector end is operable to securely couple to an overmold region of the first tube or to the second tube; and
the second connector end defining an internal conduit sized to receive the third tube such that the third tube can be matingly inserted into the second connector end wherein:
the first and second connector ends are configured for enteral applications according to American National Standards Institute standards ANSI/AAMI ID54: 1996(R) 2005; and
the first and second connector ends are sized and shaped to not matingly engage with a Luer fitting.

2. The fluid delivery system of claim 1 wherein the first tube is made of a first specified material and wherein the second and third tubes are made of a second specified material that comprises one of medical PVC or polyurethane.

3. The fluid delivery system of claim 2 wherein the first specified material comprises a silicon based tubing material.

4. The fluid delivery system of claim 1 wherein the second connector end is a female connector end sized to receive the third tube and wherein the second connector end internal conduit has a diameter of 0.185 inches.

5. The fluid delivery system of claim 1 wherein the barbed connector is permanently coupled to either of the first or second tubes made of the first or second specified materials, respectively.

6. The fluid delivery system of claim 1 further including a flange extending outward and radially from the first and second connector ends.

7. A fluid delivery system, comprising:
at least one of a first tube and a second tube;
a third tube;
a connector for use in enteral feeding applications having only a first connector end and a second connector end and further including a permanently attached cap that may be used to cover one of the first and second connector ends; and
wherein:
the first connector end is a tapered projection having only a single barb extending therefrom and is shaped and sized to:
be inserted into an overmold region of the first tube to securely mate with the first tube wherein the overmold region is characterized by a portion that includes a radius that increases from a first end of the portion to a second end of the portion; and
define a conduit sized to receive the second tube wherein the first connector end is shaped and sized to comply with standards for enteral feeding systems including American National Standards Institute standards ANSI/AAMI ID54:1996(R) 2005 and to not matingly engage with devices made according to standards for I.V. delivery of medication including ANSI/HIMA MD70.1, ISO 594/1 and ISO 594/2 standards for intravenous ports and connectors; and
the second connector end is sized to receive the third tube for enteral feeding systems.

8. The fluid delivery system of claim 7 wherein a shape of the second connector end is not able to mate with and hold a Luer fitting.

9. The fluid delivery system of claim 7 wherein the first connector end is sized to couple to the second tube wherein the second tube defines an internal conduit sized to support a specified flow rate.

10. The fluid delivery system of claim 7 further including a flange, wherein the first and second connector ends extend outward from the flange.

11. A fluid delivery system, comprising:
at least one of a first tube and a second tube;
a third tube;
a connector having only two connector ends, wherein:
a first connector end is a tapered projection having only a single barb extending therefrom and is shaped and sized to be inserted into an overmold region of the first tube to securely mate with the first tube wherein the overmold region is characterized by a portion that includes a radius that increases from a first end of the portion to a second end of the portion;
the first connector end defines an inner passageway that is sized to receive the second tube and wherein the first connector end meets standards for enteral feeding systems including American National Standards Institute standards ANSI/AAMI ID54:1996(R) 2005 and is further sized to not matingly engage with devices made according to standards for I.V. delivery of medication including ANSI/HIMA MD70.1, ISO 594/1 and ISO 594/2 standards for intravenous ports and connectors; and
the first connector end is sized and shaped to not matingly engage a syringe for I.V. delivery of medication with a Luer connector; and
a second connector end disposed in an anti-parallel manner in relation to the first connector end, the second connector end defining an inner opening with a 0.185 inch diameter and a shape that cannot matingly receive and hold a male end of an I.V. syringe that has a Luer connector and
is shaped and sized to receive the third tube or a connector that is attached to the third tube for enteral feeding systems and to comply with enteral applications according to the American National Standards Institute standards ANSI/AAMI ID54:1996(R) 2005.

12. The fluid delivery system of claim 11 wherein one of the tubes is characterized by a specified flow rate that limits the rate that fluids are delivered to the patient.

13. A fluid delivery system, comprising:
a first tube for enteral feeding systems made according to American National Standards Institute standards ANSI/AAMI ID54:1996(R) 2005; and
a connector further comprising:
a first barbed connector end defining an internal conduit sized to receive the first tube having a specified outer diameter such that the first tube can be matingly inserted into the first connector end of the connector wherein the first connector end is further sized to not matingly engage with devices made according to standards for I.V. delivery of medication including ANSI/HIMA MD70.1, ISO 594/1 and ISO 594/2 standards for intravenous ports and connectors;
a second connector end disposed in an anti-parallel manner in relation to the first connector end, the second connector end defining an outer diameter, a wall thickness, and a passageway having a 0.185 inch diameter that:
is further sized to not mate with or engage connectors made according to standards for I.V. delivery of medication including ANSI/HIMA MD70.1, ISO 594/1 and ISO 594/2 standards for intravenous ports and connectors; and a cap permanently connected to the connector for placement over one of the first and second connector ends; and a second tube for enteral feeding systems made according to American National Standards Institute standards ANSI/AAMI ID54:1996(R) 2005 for connecting to the second connector end.

14. The fluid delivery system of claim 13 further wherein the second connector end is sized to matingly engage with a second connector that is sized to not matingly engage connectors made according to standards for I.V. delivery of medication including ANSI/HIMA MD70.1, ISO 594/1 and ISO 594/2 standards for intravenous ports and connectors.

15. The fluid delivery system of claim 13 further wherein the second connector end defines an internal conduit sized to receive the second tube having a specified outer diameter such that the second tube matingly engages the internal conduit of the second connector.

16. The fluid delivery system of claim 15 wherein at least one of the first and second tubes is a silicon based tubing material.

17. The fluid delivery system of claim 15 wherein at least one of the first and second tubes is made of one of a medical PVC or polyurethane.

* * * * *